United States Patent [19]
Ding et al.

[11] Patent Number: 5,550,163
[45] Date of Patent: Aug. 27, 1996

[54] METHOD FOR REDUCING FILTRATE WASTE IN A MANUFACTURING PROCESS OF A PHARMACEUTICAL PRODUCT CONTAINING BENZALKONIUM CHLORIDE

[75] Inventors: Shulin Ding, Irvine; Robert J. Pallo, Laguna Niguel; Walter L. Tien, Irvine; Orest Olejnik, Trabuco Canyon, all of Calif.

[73] Assignee: Allergan, Inc., Irvine, Calif.

[21] Appl. No.: 285,079

[22] Filed: Aug. 3, 1994

[51] Int. Cl.⁶ .................................................. A61K 31/14
[52] U.S. Cl. ........................... 514/643; 564/282; 564/288
[58] Field of Search ..................................... 564/262, 288; 514/643

[56] References Cited

PUBLICATIONS

"A Quantitative Analysis of Preservative Adsorption on Microfiltration Membranes" Brose & Henricksen; Pharmacetical Tech. pp. 64–72 Mar. 1994.

*Primary Examiner*—Peter O'Sullivan
*Attorney, Agent, or Firm*—Walter A. Hackler

[57] ABSTRACT

A method for reducing filtrate waste in a manufacturing process of a pharmaceutical product containing benzalkonium chloride as a preservative generally includes the steps of mixing the non-benzalkonium chloride components with benzalkonium chloride to formulate the product and thereafter sterilizing the product by passing same through a microfiltration membrane. In processes in which the product has a time dependent benzalkonium chloride content due to benzalkonium chloride adsorption on a microfiltration membrane, an amount of benzalkonium chloride wasted can be reduced by maintaining a selected temperature of the microfiltration membrane and the product therein.

13 Claims, 1 Drawing Sheet

METHOD FOR REDUCING FILTRATE WASTE IN A MANUFACTURING PROCESS OF A PHARMACEUTICAL PRODUCT CONTAINING BENZALKONIUM CHLORIDE

The present invention generally relates to a method useful in the manufacture of a pharmaceutical product and is more particularly suited for reducing filtrate waste and reducing the loss of benzalkonium chloride in a manufacturing process of an ophthalmic product.

Most pharmaceutical products, including liquid ophthalmic products, typically contain antimicrobial agents to destroy or impede the growth of microorganisms. In this regard, an acceptable antimicrobial agent is benzalkonium chloride which meets the general regulatory requirements for a preservative in ophthalmic preparations.

To ensure stability of the product, a manufacturing process typically includes sterilization of the formulated product by microfiltration before packaging it into desired quantities, which may be, for example, unit doses.

Unfortunately benzalkonium chloride has a recognized adsorption affinity for microfiltration membranes commonly used for sterilization of pharmaceutical products.

Since a great number of pharmaceutical products utilizing benzalkonium chloride are manufactured in a batch process manner, a benzalkonium chloride affinity for adsorption on a filter produces what can be called filtration waste.

In the start-up of a batch process, the product does not achieve the desired benzalkonium chloride content until after a benzalkonium chloride binding equilibrium is achieved in the microfiltration membrane. Consequently, all product having below a desired benzalkonium chloride content produced during a first passage of the product through the microfiltration membrane must be either discarded or recycled, either option contributing significantly to the overall cost of the batch of product produced.

This problem is further compounded by the fact that it is desirable to formulate ophthalmic products having lower benzalkonium chloride concentrations to minimize ocular irritation or toxicity caused by the preservative. This, however, leads to even greater filtration waste because at lower benzalkonium chloride concentrations, a microfiltration membrane takes longer, and concomitant greater volume passing therethrough, to reach benzalkonium chloride binding equilibrium. Naturally, this results in greater filtration waste, which must be either thrown out or recycled.

This phenomenon, benzalkonium chloride adsorption on microfiltration membranes, therefore significantly contributes not only to increased cost of pharmaceutical products but introduces uncertainty in the manufacture of products utilizing benzalkonium chloride.

The present invention sets forth a manufacturing step which significantly reduces this uncertainty and reduces filtrate waste, thereby reducing the costs of product manufacture of many pharmaceutical products which incorporate benzalkonium chloride as a preservative.

SUMMARY OF THE INVENTION

The present invention provides for a method to reduce filtrate waste in the manufacturing process of a pharmaceutical product containing benzalkonium chloride as a preservative. Such a manufacturing process generally includes the steps of storing product components, mixing the product components, and dispensing the product to containers. As specifically directed thereto, the present invention comprises the steps of mixing non-benzalkonium chloride components with benzalkonium chloride to formulate the product. Thereafter, the product is sterilized by passing the product through a microfiltration membrane. In this regard, the product has a time dependent benzalkonium chloride content with said time dependence directly related to the benzalkonium chloride adsorption equilibration time in the microfiltration membrane.

Importantly, in accordance with the present invention, a selected temperature of both the microfiltration membrane and the product therein is maintained in order to reduce the benzalkonium chloride equilibrium time. This results in reduced filtration waste.

Further, the method in accordance with the present invention may include prefiltering all non-benzalkonium chloride product components or post filtering of the product in order to remove particulates. Alternatively, post filtering may be used. Prefiltering may be used because particulates may create more benzalkonium binding sites in the microfilter which may effectively increase the benzalkonium chloride adsorption equilibrium time in the microfiltration membrane.

The present invention provides for maintaining a microfiltration membrane temperature in order to control the benzalkonium chloride adsorption on the microfiltration membrane. This, as hereinabove set forth, significantly reduces filtration waste and produces a more certain benzalkonium chloride content product at an earlier time in a batch manufacturing process.

More particularly, a method in accordance with the present invention provides for maintaining the temperature of the microfiltration membrane and the product above room temperature, i.e., about 23° C. More preferably, the method in accordance with the present invention maintains the microfiltration membrane and product at a temperature above about 38° C.

BRIEF DESCRIPTION OF THE DRAWINGS

The advantages and features of the present invention will be better understood by the following description when considered in conjunction with the accompanying drawings in which.

DETAILED DESCRIPTION

As hereinabove noted BAK adsorption on microfiltration membranes is a well-known phenomenon. As reported by Brose and Henricksen in *Pharmaceutical Technology*, March 1994 issue, at pages 64–72, the amount of BAK adsorbed onto a membrane is a function of BAK concentration, membrane type, membrane pore size, and membrane area. A summary of BAK adsorptivity as a function of membrane type is summarized in Table I as reported by Brose and Henricksen.

This data is based on testing which included feeding a preservative-containing solution through a membrane until the preservative concentration in the filtrate was equal to that of the feed solution, indicating that adsorption in the membrane was at equilibrium. Preservative solutions that contain from 0.02 to 0.25 wt/vol % BAK were used in the experiments. Specific adsorptivity was determined by dividing the mass of the adsorbed preservative by the membrane area, resulting in a value that has units of µg/cm$^2$. The results of BAK adsorption tests of the four commercially available microfiltration membranes Brose and Henricksen are summarized in Table I.

TABLE I

| Membrane | Size (cm$^2$) | BAK Adsorptivity (µg/cm$^2$) | Filtrate Wasted (mL) |
| --- | --- | --- | --- |
| 0.2 µm PS | 500 | 63 | 135 |
| 0.22 µm PVDF | 500 | 31 | 98 |
| 0.2 µm nylon | 500 | 101 | 164 |
| 0.8 µm CA | 500 | 29 | 100 |

(PS = polysulfone, PVDF = polyvinylidene difluoride, CA = cellulose acetate

Table I shows two results for these tests: the specific BAK adsorptivity of the filters and the volume of solution filtered before the concentration of the filtrate reaches 90% of the BAK concentration in the feed. This quantity is termed "filtrate wasted" because it represents the approximate amount of filtrate that would need to be thrown away or recycled in a pharmaceutical application.

The applicants have discovered yet another factor important in reducing the loss of benzalkonium chloride in the manufacture of suitable product heretofore not recognized. Specifically, the applicants have discovered that the benzalkonium chloride equilibrium time in a microfiltrate membrane may be reduced by maintaining a select temperature in the microfiltrate membrane and the product therein. The select temperature, as hereinafter discussed in greater detail, is a temperature at or above room temperature and preferably above about 38° C.

Figure 1:
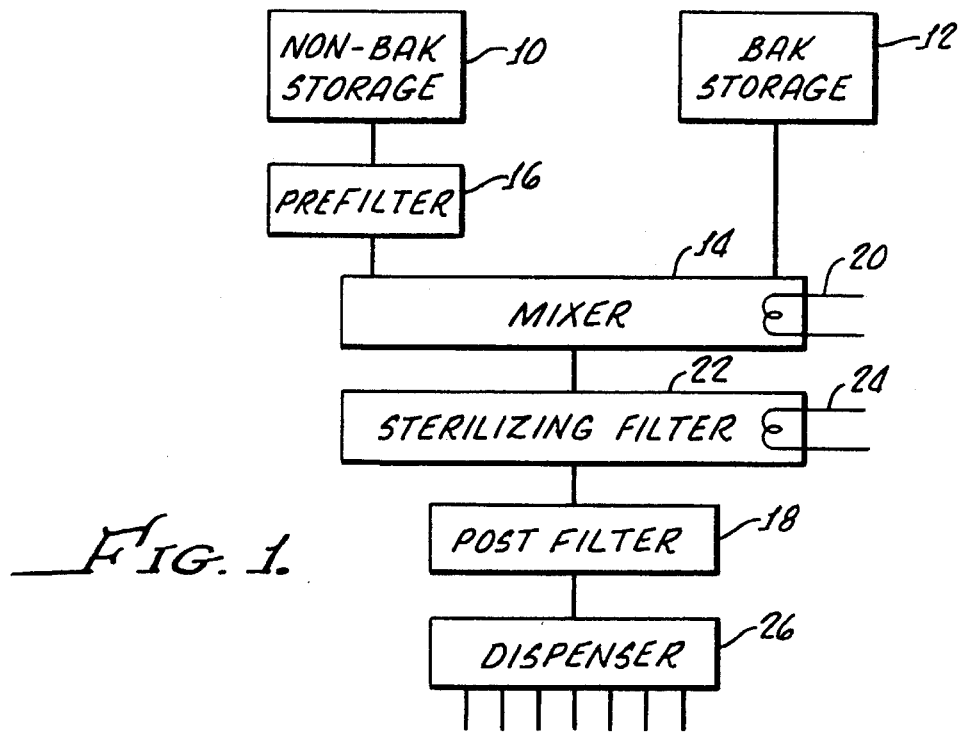
FIG. 1 is a block diagram illustrating the method of the present invention.

Turning now to FIG. 1, there is shown in block diagram form a method for reducing filtrate waste in a manufacturing process of a pharmaceutical product containing benzalkonium chloride as a preservative.

As shown in FIG. 1, non-BAK product components are stored separately in a tank 10 with a separate storage facility 12 provided for the BAK preservative. Prior to mixing the non-BAK components with the BAK in a mixer 14, the non-BAK components may be routed through a prefilter 16 in order to remove any particulate matter therein. This contributes to reducing filtrate waste in combination with the other steps of the present invention by eliminating particles which may be trapped in the sterilizing filter which provide additional adsorption sites for BAK and consequently increasing the binding equilibrium time of the membrane. Alternatively, the product may be passed through a post filter 18.

The non-BAK components are mixed or blended in a conventional manner in the mixer 14 in which the temperature of the mixed product is maintained by a conventional heater, or the like, as represented by the coil 20.

After mixing, the product is passed through a sterilizing filter 22, such as that described in the Brose and Henricksen report, which is incorporated herewith by this specific reference thereto for the purpose of describing membranes suitable for use in the method of the present invention. The filter 22 and product there in are also maintained at the select temperature by a conventional heater or the like as represented by the coil 24.

Following sterilization, the product is routed to a conventional dispenser 26 for producing product.

The manufacturing process, as hereinabove set forth and illustrated in FIG. 1, confirms the findings hereinabove reported regarding the adsorption of BAK on the filter media, particularly with regard to preservative concentration, membrane type and flow rates.

Figure 2:
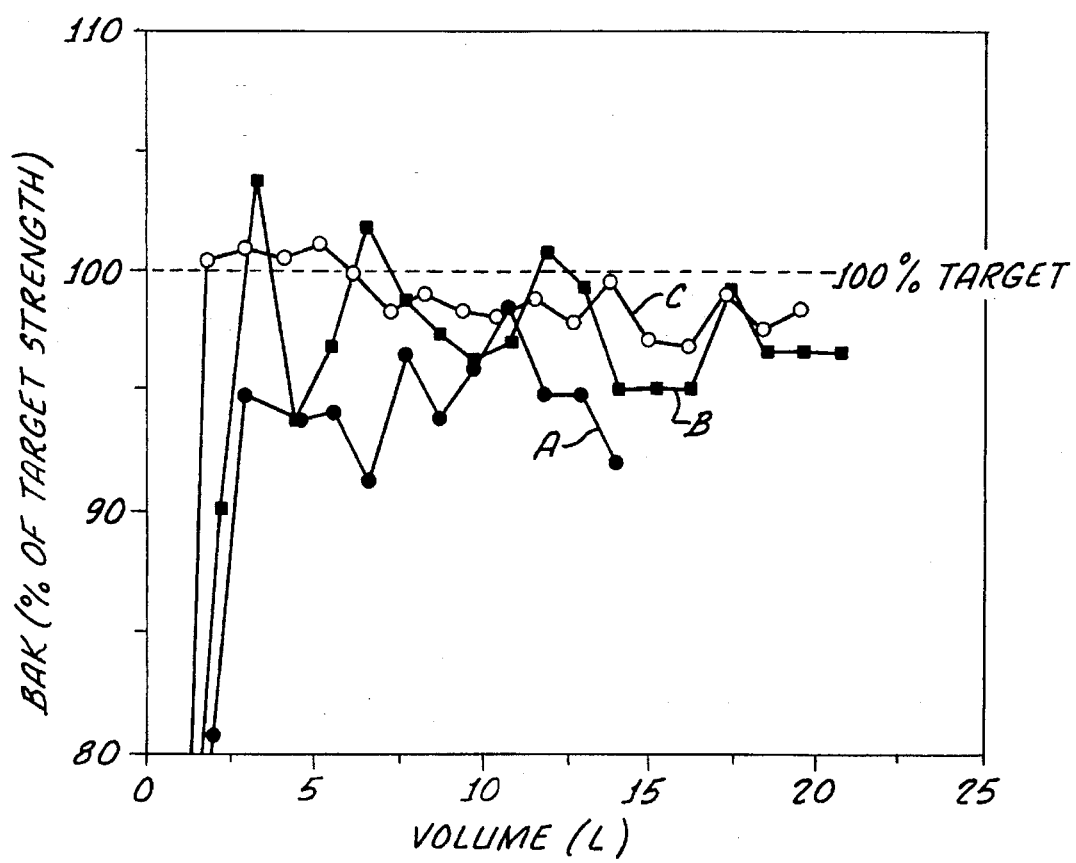
FIG. 2 is a plot of benzalkonium chloride (BAK) as a function of volume passing through a microfiltration membrane illustrating the temperature effect on BAK equilibrium in the microfiltration membrane as a function of temperature.

However, it has been found, as shown in FIG. 2, that BAK binding equilibrium can be established sooner by maintaining the filter at temperatures above room temperature and preferably considerably above room temperature, namely, 38° C. This is evident from the curves shown in FIG. 2 in which the amount of BAK in the filtrate is plotted vs. volume of product passing through the sterilization filter 22 for various target amounts of BAK product. Curve A represents the BAK concentration at a filter temperature of about 8° C.; curve B represents the BAK concentration at a filter temperature of about room temperature, or 23° C.; and curve C represents the BAK concentration at an elevated temperature of 38° C.

It is apparent from FIG. 2 that curves B and C cross the 100% target line well in advance of curve A. The target of BAK may be, for example, 100 ppm, 50 ppm, or 30 ppm.

As hereinabove discussed, it is desirable to formulate ophthalmic products at lower BAK concentrations, but lower BAK concentrations result in greater filter waste because it takes longer to reach filter equilibrium.

The results shown in FIG. 2 have been normalized and represent averages of tests run on various target concentrations of BAK from 30 ppm to 100 ppm. Benzalkonium chloride adsorption on the microfilter membrane is controlled which results in lower filtrate waste.

Although there has been hereinabove described a method for reducing filtrate waste in a manufacturing process of a pharmaceutical product in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A method for reducing filtrate waste in a manufacturing process of a pharmaceutical product containing benzalkonium chloride as a preservative, said manufacturing process including the steps of storing product components, mixing the product components and dispensing product to containers, said method comprising the steps of:

mixing the non-benzalkonium chloride components with benzalkonium chloride to formulate the product;

sterilizing the product by passing same through a microfiltration membrane, said product having a time dependent benzalkonium chloride content, the time dependence being dependent on benzalkonium chloride adsorption equilibration in the microfiltration membrane; and reducing a benzalkonium chloride equilibration time in the microfiltration membrane by maintaining a selected temperature of the microfiltration membrane and the product therein.

2. The method according to claim 1 wherein the microfiltration membrane is maintained at room temperature.

3. The method according to claim 1 wherein the microfiltration membrane is maintained above room temperature.

4. The method according to claim 1 wherein the microfiltration membrane is maintained above about 23° C.

5. The method according to claim 4 wherein the microfiltration membrane is maintained above about 38° C.

6. The method according to claim 1 further comprising the step of prefiltering all the non-benzalkonium chloride product components to remove particulates.

7. The method according to claim 1 further comprising the step of post filtering the product.

8. The method according to claim 5 further comprising the step of prefiltering all the non-benzalkonium chloride product components to remove particulates.

9. A method for reducing loss of benzalkonium chloride in a manufacturing process of an ophthalmic product, said manufacturing process including the steps of storing product components, mixing the product components and dispensing product to containers, said method comprising the steps of:

prefiltering all non-benzalkonium chloride product components to remove particulates;

mixing the prefiltered non-benzalkonium chloride product components with benzalkonium chloride to formulate the product;

sterilizing the product by passing same through a microfiltration membrane; and maintaining a microfiltration membrane temperature in order to control benzalkonium chloride adsorption on the microfiltration membrane.

10. The method according to claim 9 wherein the microfiltration membrane is maintained at room temperature.

11. The method according to claim 9 wherein the microfiltration membrane is maintained above room temperature.

12. The method according to claim 9 wherein the microfiltration membrane is maintained above about 23° C.

13. The method according to claim 12 wherein the microfiltration membrane is maintained above about 38° C.

* * * * *